United States Patent
Ueda et al.

(10) Patent No.: US 9,983,165 B2
(45) Date of Patent: May 29, 2018

(54) NITROGEN OXIDE DECOMPOSITION MATERIAL AND USE THEREOF

(71) Applicants: JAPAN FINE CERAMICS CENTER, Nagoya-shi, Aichi (JP); TOYOTA JIDOSHA KABUSHIKI KAISHA, Toyota, Aichi-ken (JP)

(72) Inventors: Taro Ueda, Nishisonogi-gun (JP); Seiji Takahashi, Ichinomiya (JP); Toyoharu Kaneko, Susono (JP); Tatsuhiro Hashida, Susono (JP); Keiichiro Aoki, Sunto-gun (JP)

(73) Assignees: JAPAN FINE CERAMICS CENTER, Nagoya-shi (JP); TOYOTA JIDOSHA KABUSHIKI KAISHA, Toyota (JP)

( * ) Notice: Subject to any disclaimer, the term of this patent is extended or adjusted under 35 U.S.C. 154(b) by 393 days.

(21) Appl. No.: 14/772,562

(22) PCT Filed: Mar. 4, 2014

(86) PCT No.: PCT/JP2014/055506
§ 371 (c)(1),
(2) Date: Dec. 30, 2015

(87) PCT Pub. No.: WO2014/136792
PCT Pub. Date: Sep. 12, 2014

(65) Prior Publication Data
US 2016/0123920 A1  May 5, 2016

(30) Foreign Application Priority Data
Mar. 6, 2013  (JP) ................................. 2013-043720

(51) Int. Cl.
*G01N 27/407* (2006.01)
*B01D 53/86* (2006.01)
(Continued)

(52) U.S. Cl.
CPC ......... *G01N 27/4075* (2013.01); *B01D 53/32* (2013.01); *B01D 53/326* (2013.01);
(Continued)

(58) Field of Classification Search
CPC .............. B01J 23/002; B01J 2523/3706; B01J 2523/24; B01J 2523/22; B01J 2523/23;
(Continued)

(56) References Cited

U.S. PATENT DOCUMENTS 5,562,888 A  10/1996 Rajadurai
6,238,816 B1  5/2001 Cable et al.
(Continued)

FOREIGN PATENT DOCUMENTS

EP  2208557 A1  7/2010
JP  H04-108667 A  4/1992
(Continued)

OTHER PUBLICATIONS

JPO computer-generated English language translation of JP 2010-261855 A. Downloaded Dec. 14, 2017. (Year: 2010).*
(Continued)

*Primary Examiner* — Alexander S Noguerola
(74) *Attorney, Agent, or Firm* — Oliff PLC (57) ABSTRACT

The present teaching rekates to providing a NOx decomposition agent having an excellent NOx decomposition rate. The NOx decomposition agent containing a perovskite oxide represented by $ABx-1MxO_3$, wherein A represents one or more elements selected from the group consisting of La, Sr, Mg, Ca and Ba, B represents Mn, M represents a combination of one or more first metal elements selected from the group consisting of Ti, Zr, Hf, Nb, Ta, Cr, Mo, W and Ce, and one or two second metal elements selected from the group consisting of Ca and Mg, and x represents a number greater than or equal to 0 and less than 1.

13 Claims, 6 Drawing Sheets (51) Int. Cl.
 B01D 53/32 (2006.01)
 B01D 53/94 (2006.01)
 B01J 23/00 (2006.01)
 B01J 23/34 (2006.01)
 G01N 31/10 (2006.01)
 G01N 33/00 (2006.01)

(52) U.S. Cl.
 CPC ..... B01D 53/8628 (2013.01); B01D 53/9422 (2013.01); B01J 23/002 (2013.01); B01J 23/34 (2013.01); B01D 2255/1021 (2013.01); B01D 2255/204 (2013.01); B01D 2255/2045 (2013.01); B01D 2255/2047 (2013.01); B01D 2255/2061 (2013.01); B01D 2255/2063 (2013.01); B01D 2255/2073 (2013.01); B01D 2255/20715 (2013.01); B01D 2255/402 (2013.01); G01N 31/10 (2013.01); G01N 33/0037 (2013.01); Y02A 50/245 (2018.01)

(58) Field of Classification Search
 CPC ............ B01J 2523/25; B01D 53/8625; B01D 53/8628; G01N 27/4074; G01N 27/4075; G01N 33/0037
 See application file for complete search history.

(56) References Cited

U.S. PATENT DOCUMENTS

| | | | | |
|---|---|---|---|---|
| 6,835,689 | B1* | 12/2004 | He | B01J 23/002 502/302 |
| 6,919,047 | B1* | 7/2005 | He | B01D 53/90 422/122 |
| 2007/0184311 | A1 | 8/2007 | Ohkubo | |
| 2008/0006532 | A1 | 1/2008 | Mukundan et al. | |
| 2008/0241681 | A1 | 10/2008 | Ito et al. | |
| 2012/0046163 | A1 | 2/2012 | Ifrah et al. | |

FOREIGN PATENT DOCUMENTS

| | | | |
|---|---|---|---|
| JP | H07-296839 | A | 11/1995 |
| JP | 2004-156504 | A | 6/2004 |
| JP | 2008-214159 | A | 9/2008 |
| JP | 2008-307492 | A | 12/2008 |
| JP | 2009-090448 | A | 4/2009 |
| JP | 2010-261855 | A | 11/2010 |
| JP | 2012-177622 | A | 9/2012 |
| WO | 2005/001980 | A1 | 1/2005 |
| WO | 2006/036838 | A2 | 4/2006 |

OTHER PUBLICATIONS

Apr. 22, 2014 Search Report issued in International Patent Application No. PCT/JP2014/055506.
Apr. 22, 2014 Written Opinion issued in International Patent Application No. PCT/JP2014/055506.
Feb. 24, 2015 International Preliminary Report on Patentability issued in International Patent Application No. PCT/JP2014/055506.
Shao, Jing et al., "Enhancement of NOx removal performance for (La0.85Sr0.15)0.99MnO3/Ce0.9Gd0.1O1.95 electrochemical cells by NOx storage/reduction adsorpton layers," Electrochimica Acta, vol. 90, pp. 482-491, (2013).
Jul. 12, 2016 Office Action issued in Japanese Patent Application No. 2013-043720.
Aug. 4, 2016 Office Action issued in Chinese Patent Application No. 201480012379.6.
Dec. 16, 2016 Extended European Search Report issued in European Patent Application No. 14761204.8.

* cited by examiner

NITROGEN OXIDE DECOMPOSITION MATERIAL AND USE THEREOF

TECHNICAL FIELD

The present specification relates to a device for nitrogen oxide decomposition, a method for nitrogen oxide decomposition, and the like.

The present application is related to Japanese Patent Application No. 2013-043720 filed on Mar. 6, 2013. The present application is based on and claims convention priority to the Japanese patent application. The entire disclosure of the Japanese patent application is herein incorporated by reference.

BACKGROUND ART

Various studies have been conducted on decomposition devices for use to decompose, for example, nitrogen oxides (hereinafter, simply called NOx sometimes) such as nitrogen monoxide and nitrogen dioxide contained in automobile emissions and the like. For example, it was reported that use of an electrode containing solid electrolytes on which nanometer-sized noble metals are highly dispersed achieves high NOx cleaning efficiency (about 80%) (Patent Document 1); a study shows that an electrode reaction area is enlarged by electronic conductors highly dispersed on solid electrolytes that are ionic conductors (Patent Document 2). It was further reported that a configuration in which substances having mixed conductivity, namely, substances having both ionic conductivity and electronic conductivity are arranged on ionically-conductive solid electrolytes can achieve highly selective NOx decomposition (Patent Document 3).

Another report shows that adopting an La-based perovskite oxide as a NOx-decomposition material allows selective detection of NOx with high sensitivity even in the presence of oxygen (Patent Document 4).

CITATION LIST

Patent Literature

Patent Document 1: Japanese Patent Application Publication No. 2009-90448 (JP 2009-90448 A)
Patent Document 2: Japanese Patent Application Publication No. 2008-307492 (JP 2008-307492 A)
Patent Document 3: Japanese Patent Application Publication No. 2004-156504 (JP 2004-156504 A)
Patent Document 4: Japanese Patent Application Publication No. 2010-261855 (JP 2010-261855 A)

SUMMARY OF INVENTION

However, the decomposition device described in Patent Document 1 has low power usage effectiveness and the decomposition devices described in Patent Documents 2 and 3 have insufficient selectivity in NOx decomposition. The NOx sensor material described in Patent Document 4 can selectively decompose NOx in the presence of excess oxygen and can detect NOx with high sensitivity, but further improvement in the decomposing activity (catalytic activity) and the detection sensitivity is demanded.

An object of the present specification is to provide a NOx-decomposition material having excellent decomposition activity and excellent detection sensitivity, a NOx decomposition device, and use thereof.

Solution to Problem

The inventors of the present invention conducted various studies on perovskite oxides for the purpose of achieving the object and, as a result, found that substituting a metallic element at a center of a cubic system of a perovskite structure with a combination of metallic elements, namely, a metallic element having a valence greater than the valence 3+ of La and a metallic element having a valence smaller than the valence 3+ of La improves NOx decomposition activity, that is, catalytic activity to selectively decompose NOx. Based on these findings, the disclosure of the present specification is provided.

(1) A NOx decomposition agent, comprising a perovskite oxide represented by:

$AB_{1-x}M_xO_3$, wherein
A represents one, two, or more kinds selected from the group consisting of La, Sr, Mg, Ca, and Ba,
B represents one, two, or more kinds selected from the group consisting of Ni, Fe, Co, Mn, Cr, and Cu,
M represents a combination of one, two or more first metallic elements selected from the group consisting of Ti, Zr, Hf, Nb, Ta, Cr, Mo, W, and Ce, and one or two second metallic elements selected from the group consisting of Ca and Mg, the combination having a molar ratio of the first metallic element to the second metallic element such that a charge of the first metallic element and a charge of the second metallic element balance out each other, and
x represents a number greater than 0 and less than 1.
(2) The Nox decomposition agent according to (1), wherein B represents Mn.
(3) The NOx decomposition agent according to (1) or (2), wherein M represents a combination of Ce and Mg.
(4) The NOx decomposition agent according to any one of (1) to (3), wherein x represents a number equal to or less than 0.2.
(5) The NOx decomposition agent according to (4), wherein
A represents La and Sr,
B represents Mn, and
M represents a combination of Ce and Mg.
(6) A NOx sensor, comprising:
an electrochemical cell that comprises:
(a) a solid electrolyte;
(b) a first electrode that comprises a NOx decomposition catalytic phase containing a perovskite oxide represented by $AB_{1-x}M_xO_3$, the first electrode being exposed to a NOx-containing gas; and
(c) a second electrode that is located to face the first electrode via the solid electrolyte interposed therebetween, the second electrode being kept from coming into contact with the NOx-containing gas;
wherein
the first electrode comprises the NOx decomposition catalytic phase that is essentially composed of the perovskite-type oxide represented by $AB_{1-x}M_xO_3$, wherein
A represents one, two, or more kinds selected from the group consisting of La, Sr, Mg, Ca, and Ba,
B represents one, two, or more kinds selected from the group consisting of Ni, Fe, Co, Mn, Cr, and Cu,
M represents a combination of one, two, or more first metallic elements selected from the group consisting of Ti, Zr, Hf, Nb, Ta, Cr, Mo, W, and Ce, and one or two second metallic elements selected from the group consisting of Ca and Mg, the combination having a molar ratio of the first metallic element to the second metallic element such that a charge of the first metallic element and a charge of the second metallic element balance out each other, and x represents a number greater than 0 and less than 1, and the first electrode keeps the solid electrolyte from coming into contact with the NOx-containing gas.

(7) The sensor according to (6), wherein the first electrode consists of the NOx decomposition catalytic phase.

(8) The sensor according to (6) or (7), wherein the first electrode is configured to be capable of being exposed to the NOx-containing gas of which oxygen concentration is not controlled.

(9) The sensor according to any one of (6) to (8), further comprising a temperature controller configured to control a temperature of the electrochemical cell to a predetermined temperature of equal to or greater than 400° C. and equal to or less than 800° C.

(10) A NOx decomposition device, comprising:
an electrochemical cell that comprises:
(a) a solid electrolyte;
(b) a first electrode that comprises a NOx decomposition catalytic phase containing a perovskite oxide represented by $AB_{1-x}M_xO_3$, the first electrode being exposed to a NOx-containing gas; and
(c) a second electrode that is located to face the first electrode with the solid electrolyte interposed therebetween, the second electrode being kept from coming into contact with the NOx-containing gas; wherein the first electrode comprises the NOx decomposition catalytic phase that is essentially composed of the perovskite oxide represented by $AB_{1-x}M_xO_3$, wherein:

A represents one, two, or more kinds selected from the group consisting of La, Sr, Mg, Ca, and Ba, B represents one, two, or more kinds selected from the group consisting of Ni, Fe, Co, Mn, Cr, and Cu, M represents a combination of one, two, or more first metallic elements selected from the group consisting of Ti, Zr, Hf, Nb, Ta, Cr, Mo, W, and Ce, and one or two second metallic elements selected from the group consisting of Ca and Mg, the combination having a molar ratio of the first metallic element to the second metallic element such that a charge of the first metallic element and a charge of the second metallic element balance out each other, and x represents a number greater than 0 and less than 1, and the first electrode keeps the solid electrolyte from coming into contact with the NOx-containing gas.

(11) A method of detecting a NOx in a NOx-containing gas by using the NOx sensor according to any one of (6) to (9), the method comprising a decomposition step,
the decomposition step including decomposing NOx in the NOx-containing gas by applying a predetermined voltage between the first electrode and the second electrode of the sensor in a state where the first electrode of the electrochemical cell is exposed to the NOx-containing gas.

(12) The method according to (11), wherein the predetermined applied voltage (the absolute value thereof) is greater than 0 mV and equal to or less than 100 mV.

(13) The method according to (11) or (12), wherein
in the decomposition step, the electrochemical cell is operated at a predetermined temperature of equal to or greater than 400° C. and equal to or less than 800° C.

DESCRIPTION OF EMBODIMENTS

The following description relates to a NOx decomposition agent disclosed in the present specification and to the use thereof. By substituting a metallic element at a center of a cubic system of a perovskite structure with a combination of a metallic element having a tendency to have a valence greater than the valence of the metallic element at the center and a metallic element having a tendency to have a valence smaller than the valence of the metallic element at the center, namely, by substituting the metallic element at the center with a combination of metallic elements so as to balance out the charges, the NOx decomposition agent disclosed in the present specification can be improved in NOx decomposition activity, namely, catalytic activity to selectively decompose NOx, compared to before such substitution. Accordingly, the NOx decomposition agent disclosed in the present specification can be used to provide a high-performance NOx decomposition device and can also be used to provide a highly sensitive NOx sensor.

Figure 1:
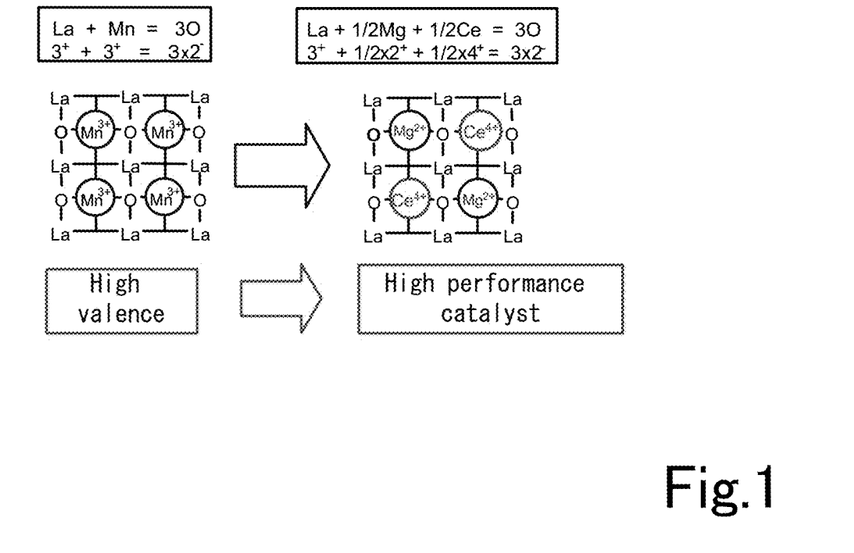
FIG. 1 is a conceptual view of a NOx decomposition agent disclosed in the present specification.

FIG. 1 is a conceptual view of the NOx decomposition agent disclosed in the present specification. In FIG. 1, $LaMnO_3$ is exemplified, and Mn (valence: 3+) that is a metallic element at the center of the perovskite structure is substituted with a combination of metallic elements, namely, Ce (valence: 4+) as a first metallic element having a valence greater than the valence of the metallic element at the center and Mg (valence: 2+) as a second metallic element having a valence smaller than the valence of the metallic element at the center. In such substitution with the combination of metallic elements, introduction of the first metallic element can improve reaction properties to NOx. Potentially but not limitative to the scope of the disclosure of the present specification, the readily changeable oxidation number of the first metallic element promotes electron exchange between the first metallic element and the second metallic element to facilitate electron movement within a NOx-decomposition material, and this promotes a NOx decomposition reaction to proceed and enhances NOx adsorptivity to eventually improve reaction properties to NOx.

Representative, non-limiting examples of the present invention will now be described in further detail with reference to the attached drawings as needed. This detailed description is merely intended to teach a person of skill in the art further details for practicing preferred aspects of the present teachings and is not intended to limit the scope of the invention. Furthermore, each of the additional features and teachings disclosed below may be utilized separately or in conjunction with other features and teachings to provide an improved nitrogen-oxide decomposition material having further improvement and the use thereof.

Moreover, combinations of features and steps disclosed in the following detailed description may not be necessary to practice the invention in the broadest sense, and are instead taught merely to particularly describe representative examples of the invention. Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Figure 2:
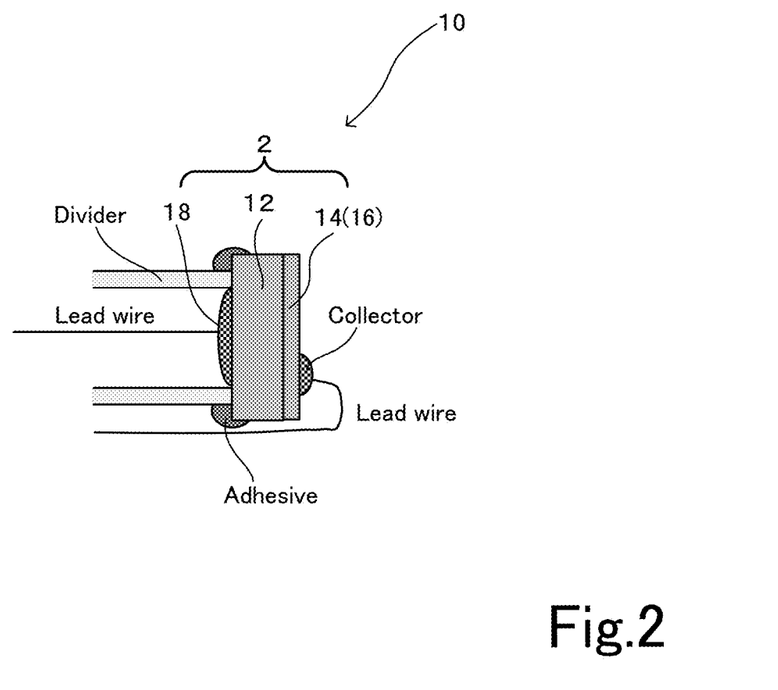
FIG. 2 schematically shows an embodiment of a NOx sensor disclosed in the present specification.

In the following, embodiments of the disclosure of the present specification are described in detail with reference to the attached drawings as needed. FIG. 2 schematically shows an embodiment of a NOx sensor of the present invention.

(NOx Decomposition Agent)

The NOx decomposition agent disclosed in the present specification contains one, two, or more perovskite oxides represented by $AB_{1-x}M_xO_3$ shown below;

$$AB_{1-x}M_xO_3.$$

In the above formula, A represents a metallic element at a vertex of a cubic system of each perovskite oxide. A may be two or more metallic elements selected from rare earth elements, alkaline-earth metal elements, and alkali metal elements. Considering formation of oxygen vacancies that contribute to NOx decomposition functions, A represents preferably one, two, or more kinds selected from the group consisting of La, Sr, Mg, Ca, and Ba. In addition, considering stability of such oxygen vacancies, A is preferably selected from La, Sr, and Mg. Furthermore, considering the amount of such oxygen vacancies, A preferably includes two kinds of elements having different valences. For example, the proportion in terms of mol % of elements having greater valences is preferably greater than the proportion in terms of mol % of the other elements having smaller valences. More specifically, when A is a perovskite oxide represented by $A1pA2qB_{x-1}M_xO_3$ in which the element A1 having a greater valence and the element A2 having a smaller valence, p is preferably equal to or greater than 0.6 and equal to or less than 0.8 and q is preferably equal to or greater than 0.2 and equal to or less than 0.4. A1 is preferably a metallic element having a valence of 3 and is typically La. A2 is a metallic element having a valence of 2 and is typically Sr and Mg.

B is a metallic element at the center of the cubic system of the perovskite oxide and preferably represents one, two, or more kinds selected from the group consisting of Ni, Fe, Co, Mn, Cr, and Cu. When the perovskite oxide has two or more elements as B, these elements to be combined are determined considering durability, oxygen ion conductivity, electronic conductivity, and catalytic activity and are preferably one, two, or more kinds selected from Ni, Fe, Co, and Mn. More preferably, B preferably has a valence of +3 and is typically Mn.

M represents an element to partly substitute B that is the metallic element at the center of the perovskite oxide. M represents a combination of the first metallic element and the second metallic element.

The first metallic element is a metallic element that tends to have a greater valence. More specifically, the first metallic element includes a metallic element the oxidation number of which readily varies within the range of +4 and greater or the range of +2 and greater. Examples of the first metallic element include one, two, or more first metallic elements selected from the group consisting of Ti, Zr, Hf, Nb, Ta, Cr, Mo, W, and Ce. The first metallic element may be selected, as needed, by a person skilled in the art by considering the kinds of the other metallic elements, namely, A and B and the kind, the valence, and the ion radius of the second metallic element or, where appropriate, by synthesizing a complex substitution to see the NOx decomposition reaction properties thereof. In particular, the first metallic element is preferably cerium (Ce) that can have a valence of either +3 or +4.

The second metallic element is a metallic element that tends to have a smaller valence, namely, that tends to have a valence smaller than the valence of the first metallic element. More specifically, examples of the second metallic element include one or two second metallic elements selected from the group consisting of Ca and Mg. The second metallic element may be selected, as needed, by a person skilled in the art by considering the kinds of the other metallic elements, namely, A and B, and the kind, the valence, and the ion radius of the first metallic element or, where appropriate, by synthesizing a complex substitution to assess the NOx decomposition reaction properties thereof. When the first metallic element is Ce, the second metallic element is preferably Mg from the viewpoints of the ion radius and the valence.

The ratio (molar ratio) of the first metallic element to the second metallic element thus combined is preferably a ratio by which the charge of the first metallic element and the charge of the second metallic element can be balanced out. More specifically, the valence of M is preferably equal to the valence of the metallic element at the B site before substitution so as to avoid a change in the total number of cations. For example, when the metal at the B site is Mn (+3), the first metallic element is Ce (+4), and the second metallic element is Mg (+2), the ratio Ce:Mg is preferably 1:1 so as to achieve an average valence of M of +3.

In the formula described above, x represents a number of greater than 0 and less than 1. x is not particularly limited and may be selected as needed by a person skilled in the art depending on the kinds of the metallic element at the A site, the metallic element at the B site, the first metallic element, and the second metallic element or, where appropriate, by synthesizing a complex substitution to assess the NOx decomposition reaction properties thereof. From the viewpoint of the stability of the crystal structure, x is preferably equal to or greater than 0.1 and equal to or less than 0.8, more preferably equal to or greater than 0.1, and more preferably equal to or less than 0.6. For example, when the metal at the A site is La and Sr and the metal at the B site is Ce and Mg, x is preferably equal to or less than 0.6, more preferably equal to or less than 0.4, and further preferably equal to or less than 0.2 from the viewpoint of substitution within the lattice.

Examples of perovskite oxides represented by $ABO_3$ include La—Sr—Ni—O perovskite oxide, La—Sr—Fe—O perovskite oxide, and perovskite oxides represented by $La_xSr_{1-x}Co_yMn_{1-y}O_3$ (0<x<1, 0≤y≤1) such as La—Sr—Co—O perovskite oxide, La—Sr—Mn—O perovskite oxide, and La—Sr—Co—Mn—O perovskite oxide. The elements at the B site of each perovskite oxide may be partly substituted with M (the first metallic element and the second metallic element). In the perovskite oxide disclosed in the present specification, it is preferable that A represents La and Sr, B represents Mn, and M represents a combination of Ce and Mg, in the formula described above.

Such a perovskite oxide can be synthesized according to a conventional procedure. Examples of the procedure include a method of mixing an aqueous solution of salts (acetic acid salts, nitric acid salts, or the like) of La and Sr and an aqueous solution of salts of the element at the B site, the first metallic element and the second metallic element, homogeneously, and then drying and sintering the resultant mixture. The method of synthesis is not particularly limited, and examples of the method include spray pyrolysis method.

(NOx Sensor)

FIG. 2 shows an embodiment of a NOx sensor 2 disclosed in the present specification. In the following, the NOx sensor is described referring to FIG. 2 as needed. The NOx sensor 2 may have an electrochemical cell 10. The electrochemical cell 10 contains a solid electrolyte 12 and at least one pair of a first electrode 14 and a second electrode 18 facing each other with the solid electrolyte 12 interposed therebetween.

NOx to be detected with the NOx sensor herein contains nitrogen oxides such as nitrogen monoxide (NO), nitrogen dioxide ($NO_2$), nitrous oxide (dinitrogen monoxide) ($N_2O$), dinitrogen trioxide ($N_2O_3$), dinitrogen tetraoxide ($N_2O_4$), and dinitrogen pentoxide ($N_2O_5$). Specifically, the NOx sensor herein preferably detects at least one or preferably both of nitrogen monoxide and nitrogen dioxide.

A NOx-containing gas to which the NOx sensor herein may be applied is simply required to contain NOx and may be various combustion gases and the like. In particular, the NOx-containing gas is preferably emissions from various mobile bodies such as automobiles because such emissions are thought to be one of the major sources of air pollutants.

(Electrochemical Cell)

(Solid Electrolyte)

The solid electrolyte 12 is not particularly limited provided that it has oxygen ion conductivity. Examples of the solid electrolyte 12 include zirconia solid electrolytes (typically, $ZrO_2$-$M_2O_3$ solid solution or $ZrO_2$-MO solid solution in which M is preferably Y, Yb, Gd, Ca, or Mg), ceria solid electrolytes (typically, $CeO_2$-$M_2O_3$ solid solution or $CeO_2$-M solid solution in which M is preferably Y or Sm), bismuth oxide solid electrolytes (typically, $Bi_2O_3$—$WO_3$ solid solution), and $LaGaO_3$ compounds having a perovskite structure. From the viewpoints of stability and oxygen ion conductivity in the case where the NOx-containing gas is emissions from internal combustion engines (engines) of automobiles and the like, zirconia solid electrolytes are preferable. Particularly preferable among these is stabilized zirconia that is a solid solution of 3 to 10 mol % of yttria, magnesia, or calcia.

(First Electrode)

The first electrode 14 is in contact with (or adhered to) the solid electrolyte 12. The first electrode 14 functions as a decomposition electrode for NOx decomposition. The first electrode 14 contains a NOx decomposition catalytic phase 16 (hereinafter, simply called a catalytic phase 16) consisting of one, two, or more materials having both oxygen ion conductivity and electronic conductivity and also having NOx decomposition catalytic activity. The first electrode preferably consists of the catalytic phase 16, and the surface thereof to be exposed to the NOx-containing gas has no coating thereon.

The catalytic phase 16 may be, for example, composed of two or more materials and is preferably composed of a single material that satisfies all the requirements described above. By using such a material, NOx decomposition can be achieved with high selectivity and high responsiveness. In other words, the catalytic phase 16 may be, for example, formed of an oxygen ion conductive material, an electronically conductive material, and a material having NOx decomposition catalytic activity, preferably contains the perovskite oxide disclosed in the present specification, more preferably essentially consists of the perovskite oxide, and further preferably substantially consists of the perovskite oxide. The perovskite oxide disclosed in the present specification has both oxygen ion conductivity and electronic conductivity and also has excellent NOx decomposition catalytic activity. Provided that the first electrode 14 contains the catalytic phase 16 that contains the perovskite oxide, when the first electrode 14 is exposed to the NOx-containing gas and voltage is applied across the electrochemical cell 10 to cause electrons to flow into the first electrode 14, the following event occurs.

(1) Flowing from an external circuit into the first electrode 14, the electrons diffuse across the catalytic phase 16 that contains the perovskite oxide.

(2) The catalytic phase 16 exposed to the NOx-containing gas allows NOx that is adsorbed thereon to preferentially react with the electrons to reduce (decomposition). $O^{2-}$ generated during reduction reaction, which has mixed conductivity diffuses across the catalytic phase 16, reaches the solid electrolyte 12 having oxygen ion conductivity, and further diffuses to reach the second electrode 18.

This event is thought to occur to perovskite oxides in common. It is thought that decomposition of NOx such as NO caused by catalytic activity of the perovskite oxide is contributed by oxygen vacancies present in the perovskite structure. Accordingly, it is thought that a NOx reduction reaction in electrochemical decomposition of NOx is also contributed by these oxygen vacancies. It is also thought that, because the perovskite oxide disclosed in the present specification has both oxygen ion conductivity and electronic conductivity and also has excellent NOx decomposition catalytic activity, the same event occurs to NOx with high selectivity even at a high oxygen concentration. It is also thought that, as a result of it, adequate capability of selective decomposition and an adequate speed of response can be ensured even at a high oxygen concentration.

The first electrode 14 may be solely composed of the catalytic phase 16 or, provided that the catalytic phase 16 is at least provided as a continuous phase, may contain the catalytic phase 16 as a matrix (mother phase) or as a disperse phase. The first electrode 14 of the decomposition device 2 of the present invention, however, contains no oxygen ion conductive materials such as solid electrolytes.

The first electrode 14 may contain noble metals such as palladium (Pd), platinum (Pt), and rhodium (Rh) provided that the capability of the catalytic phase 16 to selectively decompose NOx is not impaired.

(Second Electrode)

The second electrode 18 is in contact with (or adhered to) the solid electrolyte 12 in a way that the second electrode 18 faces the first electrode 14 with the solid electrolyte 12 interposed therebetween. The second electrode 18 is a counter electrode to the first electrode 14 that serves as a decomposition electrode, and functions as a standard electrode or a reference electrode. The second electrode 18 is simply required to be electronically conductive, and the composing material thereof is not particularly limited. Examples of an electronically conductive material include noble metals that are elements of the platinum group (typically, Pt, Pd, and Rh), other noble metals (typically, Au and Ag), highly conductive base metals (Ni, for example), and alloys based on any of these metals (Pt—Rh and Pt—Ir, for example). Further examples of an electronically conductive material include metal oxides such as nickel oxide, cobalt oxide, copper oxide, lanthanum manganite, lanthanum cobaltite, and lanthanum chromite. The second electrode 18 may contain one, two, or more kinds of such an electronically conductive material. The second electrode 18 may also contain an oxygen ion conductive material. The oxygen ion conductive material may be the same material used as the solid electrolyte 12. Examples of the oxygen ion conductive material include zirconia stabilized with yttria or with scandium oxide, ceria stabilized with gadolinium oxide or samarium oxide, and lanthanum gallate. Considering, for example, the balance with the electronic conductivity of the second electrode 18 and the balance with adhesion to the solid electrolyte 12, the content of the oxygen ion conductive material in the second electrode 18 is preferably within the range from higher than 0% by mass to equal to or less than 10% by mass and is more preferably within the range from equal to or greater than 1% by mass to equal to or less than 5% by mass relative to the total mass of the electrode 18.

(Fabrication of Electrochemical Cell)

The electrochemical cell 10 is fabricated with the solid electrolyte 12, the first electrode 14, and the second electrode 18 according to a conventional procedure. The electrochemical cell 10 may be an electrolyte supported cell or an electrode supported cell, for example. When the electrochemical cell 10 is the electrolyte supported cell, a composition for use to form the first electrode 14 is typically applied onto one surface of the solid electrolyte 12 by screen printing or the like before or after sintering, followed by sintering to form a laminate of the solid electrolyte 12 and the first electrode 14. The same procedure may be employed to form the second electrode 18 and the like on the solid electrolyte 12. Although the electrochemical cell 10 is used in various embodiments depending on the embodiment of the NOx decomposition device, the first electrode 14 is configured to always be capable of being exposed to the NOx-containing gas regardless of the embodiment of the electrochemical cell 10.

Each of the first electrode 14 and the second electrode 18 is configured to have, where appropriate, a collector consisting of a conductive material such as metals so as to allow voltage application from an external source. The NOx decomposition device of the present invention is preferably used in a state where voltage is applied between the first electrode 14 and the second electrode 18. By measuring an electric current flowing between the electrodes while voltage being applied, an amount of decomposed NOx can also be detected with high sensitivity. Therefore, a preferable embodiment for using the NOx decomposition device of the present invention is a NOx decomposition device such as a direct-type NOx decomposition device and a limiting current-type NOx decomposition device. The configuration that allows electric field application is not particularly limited, and an example thereof is that, as shown in FIG. 2, a collector consisting of Pt and the like is provided onto part of the surface of the first electrode 14 and the collector is connected to the external power source via a lead wire. In the same manner, the second electrode 18 has a lead wire connected thereto. When the second electrode 18 is formed solely of metals and the like, formation of the collector is not necessary.

The first electrode 14 is not particularly limited and may have a collector essentially composed of one, two, or more kinds selected from noble metals such as platinum (Pt), Au (gold), Ag (silver), palladium (Pd), and rhodium (Rh) and base metals.

The first electrode 14 is preferably provided to keep the solid electrolyte 12 from coming into contact with the NOx-containing gas. With this configuration, an $O_2$ reduction reaction that can occur at the interface of three phases, namely, the solid electrolyte 12, the decomposition phase 16, and the NOx-containing gas, may be inhibited or avoided and therefore a reaction of selective NOx decomposition may be maintained. By inhibiting or avoiding the $O_2$ reduction reaction that can occur at the interface of three phases, namely, the collector composed of Pt and the like and the NOx-containing gas, the reaction of selective NOx decomposition may be maintained. The first electrode 14 preferably keeps the entire area of the solid electrolyte 12 exposed to the NOx-containing gas, from coming into contact with the NOx-containing gas.

In order to have the first electrode 14 keep the solid electrolyte 12 from coming into contact with the NOx-containing gas, the first electrode 14 that is formed adhering to the solid electrolyte 12 preferably has a thickness of equal to or greater than 0.5 μm and equal to or less than 50 μm. When the thickness is within this range, adequate density can be ensured and oxygen ion conductivity can be maintained. Considering gas-blocking properties, the thickness is more preferably equal to or greater than 1 μm and equal to or less than 10 μm. Further preferably, the thickness is equal to or greater than 2 μm and equal to or less than 8 μm. The first electrode 14 having such a thickness may be subjected, for example, to the ceramic thin film production technique that includes coating with a liquid ceramic material for use to form the first electrode 14 and then carrying out drying, sintering, and the like.

Preferably, the first electrode 14 also keeps the solid electrolyte 12 from coming into contact with the collector. With this configuration, an $O_2$ reduction reaction that can occur at the interface of three phases, namely, the solid electrolyte 12, the collector, and the NOx-containing gas may be inhibited or avoided and therefore a reaction of selective NOx decomposition may be maintained. Preferably, the first electrode 14 keeps the solid electrolyte 12 from coming into contact with the NOx-containing gas continuously across the region where the collector is to be provided. Specifically, the first electrode 14 that is thick enough and/or continuous enough to avoid the collector, when provided, from reaching and coming into contact with the solid electrolyte 12 is provided to cover the side of the solid electrolyte 12 exposed to the NOx-containing gas. A cell 2 that includes the first electrode 14 having such a configuration may be obtained by forming the first electrode 14 so as to keep the solid electrolyte 12 from coming into contact with the NOx-containing gas and forming the collector on the surface of the first electrode 14.

(Embodiment of NOx Sensor)

The NOx sensor 2 disclosed in the present specification may adopt various embodiments of NOx detection (decomposition). In a typical embodiment, with voltage being applied between the first electrode 14 and the second electrode 18 in an atmosphere at a temperature adequate for the solid electrolyte 12 to exhibit oxygen ion conductivity, the first electrode 14 is exposed to the NOx-containing gas, and NOx in the NOx-containing gas is directly detected or decomposed.

The NOx sensor 2 of the present invention is thus capable of decomposing and detecting NOx even at a high oxygen concentration, and therefore can adopt a configuration where the NOx sensor 2 of the present invention is exposed to the NOx-containing gas having an oxygen concentration that is not controlled to a predetermined range in advance. The oxygen concentration in the NOx-containing gas to which the first electrode 14 in the NOx sensor 2 is exposed is not particularly limited, and is preferably equal to or greater than 0.5% and is more preferably equal to or greater than 1% so as to allow the NOx sensor 2 disclosed in the present specification to excellently sense NOx even at a high oxygen concentration. The oxygen concentration in the NOx-containing gas to which the first electrode 14 in the NOx sensor 2 is exposed can further be set at equal to or greater than 5%, more preferably equal to or greater than 10%, and further preferably equal to or greater than 15%. The upper limit to the oxygen concentration in the NOx-containing gas to which the first electrode 14 in the NOx sensor 2 is exposed is not particularly limited, and is preferably equal to or less than 21%, which is the atmospheric oxygen concentration.

The NOx sensor 2 typically adopts a configuration where the first electrode 14 is directly exposed to the NOx-containing gas and the second electrode 18 is kept from or can be kept from coming into contact with the NOx-containing gas to which the first electrode 14 is exposed. A suitable configuration of contact between the first electrode 14 of the electrochemical cell 10 and the NOx-containing gas can be obtained by providing a divider that is necessary to form a channel of the NOx-containing gas so as to ensure such a configuration of contact. The divider is preferably formed by using a material having adequate insulating properties and adequate heat resistance at a temperature range at which the NOx sensor 2 is used. Examples of the material include ceramic materials such as alumina, magnesia, mullite, and cordierite.

FIG. 2 shows an embodiment of the NOx sensor 2 of a direct detection (decomposition) type. In the embodiment shown in FIG. 2, a divider that separates the space accommodating the second electrode 18 from the space accommodating the first electrode 14 is formed on the second electrode 18 side of the solid electrolyte 12. The configuration for separating the first electrode 14 from the second electrode 18 is not limited thereto, and the divider may alternatively be formed on the first electrode 14 side of the solid electrolyte 12.

The NOx sensor 2 disclosed in the present specification has high NOx selectivity and therefore can achieve highly sensitive decomposition and detection of NOx in either of a NOx-containing gas having a high oxygen concentration and the NOx-containing gas having a low oxygen concentration, regardless of the oxygen concentration in the NOx-containing gas.

Figure 3:
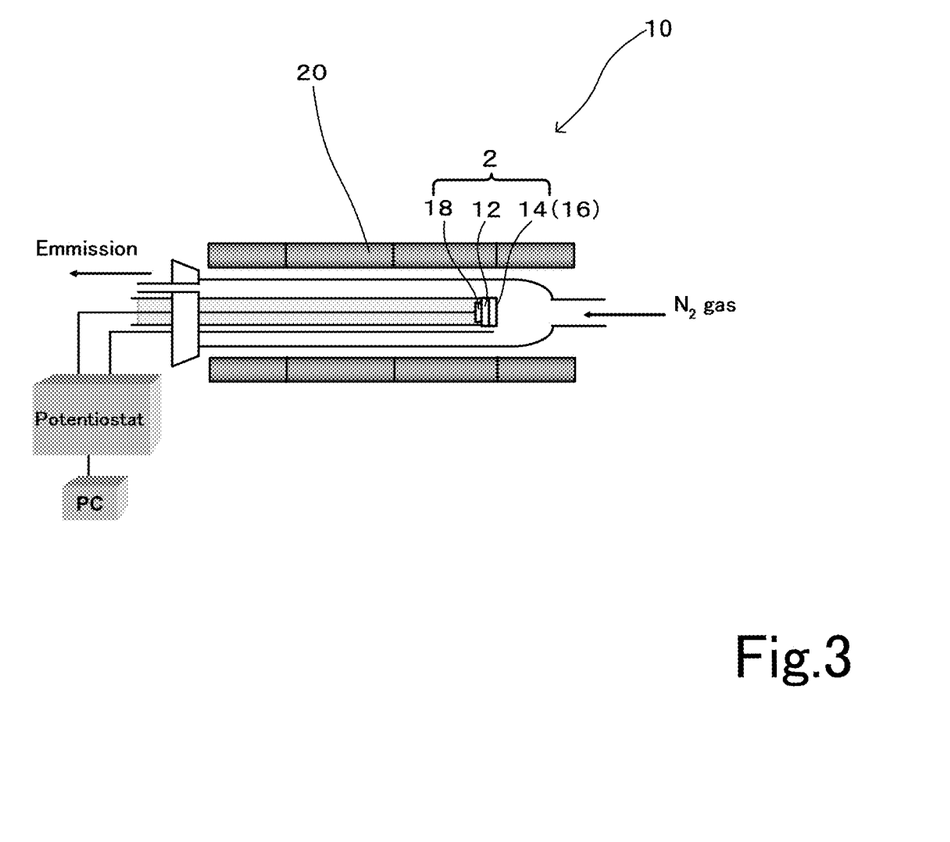
FIG. 3 shows an embodiment of NOx decomposition using a NOx sensor disclosed in the present specification.

The NOx sensor 2 disclosed in the present specification may have a temperature controller for controlling a temperature of the electrochemical cell 10. With the temperature controller provided, it is possible to suitably regulate the ion conductivity of the solid electrolyte 12 and the selectivity for NOx ($NO_2$, for example) from $O_2$ of the first electrode 14 or the electrochemical cell 10. The temperature controller has, for example, a heating (or cooling) means to heat or cool the electrochemical cell 10 or the vicinity thereof or both of the heating means and the cooling means, a temperature sensor to detect the temperature of or near the electrochemical cell 10, and a controlling circuit to produce a control signal for controlling the temperature of the electrochemical cell 10 and the like based on a signal from the temperature sensor. As shown in FIG. 3, for example, the heating means (heater) may be configured to heat a region that accommodates the electrochemical cell 10 and the NOx-containing gas reaching the electrochemical cell 10.

The temperature controller is not particularly limited and may be various known means. The temperature control achieved with the temperature controller is not particularly limited provided that it allows NOx decomposition. The electrochemical cell 10 in the NOx sensor 2 disclosed in the present specification can stably operate at equal to or greater than 400° C. and equal to or less than 800° C. Considering NOx selectivity, the temperature of and near the electrochemical cell 10 is preferably controlled to equal to or less than 750° C., more preferably equal to or less than 700° C., and further preferably equal to or less than 600° C. When the temperature of the electrochemical cell 10 or the vicinity thereof is equal to or less than 600° C., NOx selectivity of equal to or greater than 70% can be obtained. Furthermore, considering the NOx selectivity, the temperature of and near the electrochemical cell 10 is more preferably equal to or less than 550° C., further preferably equal to or less than 500° C., and even further preferably equal to or less than 450° C. Considering the ion conductivity of the solid electrolyte 12, the temperature of the electrochemical cell 10 or the vicinity thereof is preferably equal to or greater than 450° C. and is more preferably equal to or greater than 500° C. The temperature range is preferably equal to or greater than 450° C. and equal to or less than 700° C. and is further preferably equal to or greater than 450° C. and equal to or less than 600° C.

The electrochemical cell 10 can maintain the perovskite oxide structure of the catalytic phase 16 stable and exhibit its capability of selective NOx decomposition, even in a reducing atmosphere. The reducing atmosphere is an atmosphere essentially constituted of a reducing gas. Examples of the reducing gas include $SO_2$, $H_2S$, CO, NO, and CO. Typical examples of the reducing atmosphere include atmospheres essentially constituted of carbon monoxide (CO) and hydrocarbons (HCs). The electrochemical cell 10 can also maintain the structure of the perovskite oxide in the catalytic phase 16 stable in a reducing atmosphere at a high temperature of approximately 800° C. Such a reducing atmosphere can occur, for example, in engines of mobile bodies such as automobiles. Such a reducing atmosphere also tends to occur at such an air-fuel ratio that fuel is present in abundance. Accordingly, the NOx decomposition device 2 herein may be preferably used, for example, as a NOx decomposition device for use on emissions from engines of various mobile bodies.

The NOx sensor 2 disclosed in the present specification may have a voltage application means for applying voltage between the first electrode 14 and the second electrode 18. Specifically, an external circuit that allows electrons to flow into the first electrode 14 may be provided. The voltage application means may be provided to the electrochemical cell 10 via a lead wire or lead wires or the like that is provided to the electrodes 14 and 18 as described above. In addition, the voltage application means may have a potentiostat and the like for maintaining a certain voltage. The NOx decomposition device 2 of the present invention may also have a means for electric current detection such as an ammeter so as to measure an electric current flowing between the first electrode 14 and the second electrode 18.

The NOx sensor 2 disclosed in the present specification described above may be used as it is as the NOx decomposition device. The various embodiments of the NOx sensor 2 may be applied as they are as embodiments of the NOx decomposition device.

(Method of NOx Detection)

The method of NOx detection disclosed in the present specification may include the following NOx-detecting step using the NOx sensor disclosed in the present specification. That is, the method of NOx detection disclosed in the present specification may include a sensing step of applying a predetermined voltage between the first electrode 14 and the second electrode 18 in a state where the first electrode 14 of the electrochemical cell 10 is exposed to the NOx-containing gas so as to decompose NOx in the NOx-containing gas.

In the NOx-detecting step, the first electrode 14 is exposed to the NOx-containing gas. As described above, the oxygen concentration in the NOx-containing gas may vary depending on the embodiment of the NOx sensor 2. When the NOx sensor 2 disclosed in the present specification adopts an embodiment of the NOx sensor of a direct decomposition type, the oxygen concentration in the NOx-containing gas may be equal to or greater than 5% or may equal to or less than 15%. When an embodiment of a NOx sensor in which the oxygen concentration in the NOx-containing gas is limited is adopted, the oxygen concentration in the NOx-containing gas may be equal to or less than 0.01%.

In the NOx-containing gas to which the first electrode 14 is exposed, the oxygen concentration may be controlled to a predetermined concentration range. A NOx concentration in the NOx-containing gas to which the first electrode 14 is exposed, in other words, the total concentration of one, two, or more kinds of nitrogen oxide gases may be equal to or less than 1000 ppm and is preferably at least equal to or greater than 10 ppm.

The detecting step is carried out with the temperature of the electrochemical cell 10 being high enough to ensure the ion conductivity of the solid electrolyte 12. From the viewpoint of NOx selectivity, the detecting step is preferably carried out at a temperature that is described above in the description regarding the temperature controller. Namely, the temperature is preferably equal to or less than 750° C. and is more preferably equal to or less than 700° C. This is because NOx selectivity of equal to or greater than 50% can be ensured at a temperature equal to or less than 700° C. Considering NOx selectivity, the temperature is more preferably equal to or less than 600° C., further preferably equal to or less than 550° C., further more preferably equal to or less than 500° C., and most preferably equal to or less than 450° C.

In the detecting step, voltage is applied between the first electrode 14 and the second electrode 18. Specifically, the voltage is applied with an external circuit so as to feed electrons into the first electrode 14. The amount of the voltage applied (absolute value) is not particularly limited, and may be about equal to or less than 1 V, for example, and is more preferably greater than 0 mV and equal to or less than 100 mV. With a voltage within this range being applied, an adequate amount of electric current response may be obtained and selective NOx detection in an oxygen atmosphere proceeds well. Considering the amount of an electric current, the amount of the voltage applied is preferably equal to or greater than 20 mV and is further more preferably equal to or greater than 30 mV. Considering selective NOx detection, the amount of the voltage applied is further preferably equal to or less than 80 mV and is further more preferably equal to or less than 70 mV.

By carrying out the detecting step, NOx in the NOx-containing gas is decomposed and is also detected. Simultaneous measurement of the electric current value allows NOx sensing and NOx concentration measurement. Depending on the configuration of the electrochemical cell 10, sensing NOx from large excess oxygen can be achieved with high selectivity, NOx detection can be accordingly achieved while inhibiting or avoiding influence of the oxygen concentration, and the NOx concentration can be measured with precision, high accuracy, and excellent reproducibility. In addition, depending on the configuration of the electrochemical cell 10, NOx decomposition can be achieved with high NOx selectivity at an operating temperature (equal to or less than 600° C., for example) lower than operating temperatures in conventional procedures, and therefore excellent NOx sensing can be achieved at a low temperature compared to the temperatures in conventional procedures. Furthermore, when the detecting step is carried out in an embodiment of the NOx sensor of a direct decomposition type, a simplified configuration can be adopted and therefore complicated procedure of oxygen concentration control can be avoided.

The method of NOx detection disclosed in the present specification described above can be used as it is as a method of NOx decomposition. The various embodiments of the method of NOx detection can be applied as they are as embodiments of the method of NOx decomposition.

EXAMPLE

Specifics of the present invention are described below referring to an example. The present invention, however, is not limited to the examples.

Example 1

In the following example, an electrochemical cell with a NOx sensor of a direct decomposition type was fabricated. Using the NOx sensor thus fabricated, decomposition and detection of NOx were carried out under the following conditions. In other words, the electrochemical cell was fabricated in which a perovskite oxide synthesized in Example 1 served as a decomposition electrode, then the resultant cell was placed within a glass tube with an electric furnace attached thereto, subsequently a gas shown in the following table was made to flow within the glass tube, and then a potential difference was applied between the decomposition electrode and a counter electrode with the use of a potentiostat, followed by reading the amount of an electric current. The electrochemical cell was fabricated as follows.

(1) Preparation of YSZ Pellet

A YSZ powder (zirconia that was 8-mol % $Y_2O_3$ solid solution, manufactured by Tosoh Corporation) was subjected to uniaxial pressing with the use of a tablet molding device having a diameter of 10 mm, and the resultant was subjected to cold isostatic pressing (CIP), followed by sintering in an atmospheric environment at 1530° C. for 2 hours to prepare a pellet having a diameter of about 9 mm and a thickness of 1 mm.

(2) Fabrication of Decomposition Electrode and Counter Electrode

Then, one surface of the pellet thus prepared was subjected to printing with a paste of α-terpineol mixed with a perovskite oxide $(La_{0.8}Sr_{0.2}Mn_{1-x}M_xO_3$ (M:Ce:Mg (1:1), x=0.2, 0.4, and 0.6 (hereinafter, each called LSMCM01, LSMCM02, and LSMCM03) using a screen with a diameter of 7 mm. The opposite surface of the pellet was subjected to printing with a platinum paste (TR7095, manufactured by Tanaka Kikinzoku Kogyo K. K.) using a screen with a diameter of 3 mm. The resultant was subjected to sintering in the atmosphere at 1000° C. for 2 hours to form a decomposition electrode (first electrode) and a counter electrode (second electrode). Thus, an electrochemical cell was fabricated. The thickness of the decomposition electrode\ was 5 μm, which was determined so that a solid electrolyte was kept from coming into contact with a NOx-containing gas.

The perovskite oxide was synthesized as follows. Raw materials that were $La(NO_3)_3 \cdot 6H_2O$, $Sr(NO_3)_2$, $Mn(NO_3)_2 \cdot 6H_2O$, and $Mg(NO_3)_2 \cdot 6H_2O_2$ were subjected to spray pyrolysis. A starting material that was an aqueous solution dissolving the various metal nitrates was subjected to sonication to form mist, followed by being introduced into an electric tube furnace set at 800° C. Evaporation of water, thermal decomposition of metal components, and crystallization into perovskite complexes occurred in the mist at this time. The resultant powder was collected and recovered with a filter placed at the outlet.

(3) Collector Installation

To the surface of the resultant decomposition electrode of the electrochemical cell, a Pt wire was bonded using a Pt paste (TR7905, manufactured by Tanaka Kikinzoku Kogyo K. K.) according to the embodiment shown in FIG. 2, followed by sintering the Pt wire in the atmosphere at 1000° C. for 2 hours for installation of a collector and a lead wire.

(4) Installation of Magnesia Tube

As a divider to separate the decomposition electrode and the counter electrode with respect to the NOx-containing gas, a magnesia tube (MgO, outer diameter×inner diameter× length=6 mm×4 mm×350 mm) was used. The magnesia tube was bonded to the electrochemical cell with an inorganic adhesive so that the sensing electrode and the counter electrode were exposed to different gas atmospheres according to the configuration exemplified in FIG. 2. Thus, a NOx decomposition device of a direct decomposition type was fabricated.

(5) Preparation of NOx-Containing Gas

A base gas and the NOx-containing gas were prepared. The base gas was synthetic air having a composition similar to the composition of air. The NOx-containing gas was prepared by diluting 500-ppm $NO_2$ with the base gas. The concentrations of these gases were adjusted by using gas cylinders containing pure oxygen ($O_2$), pure nitrogen ($N_2$), or 1000-ppm nitrogen dioxide (a mixed gas of $NO_2$, pure nitrogen, and 1000-ppm (0.1%) $NO_2$), respectively, and adjusting the flow rate from each cylinder with a mass flow meter.

(6) Measurement Method

As in the embodiment exemplified in FIG. 3, the NOx sensor fabricated above was placed in a glass tube equipped with a flange. In the glass tube, the base gas was supplied and then the NOx-containing gas was supplied instead. While the gases flowing, a potential difference was applied between the decomposition electrode and the counter electrode using a potentiostat, followed by reading the amount of an electric current. These gases were supplied with the temperature raised to reach 500° C. with the use of a heater. The flow speed was adjusted to 100 $cm^3$/minute with a mass flow meter, and the potential difference applied was −50 mV. The results of measuring the decomposition electric current % and the electric power usage effectiveness % with the use of the NOx sensor are shown in FIG. 4.

Figure 4:
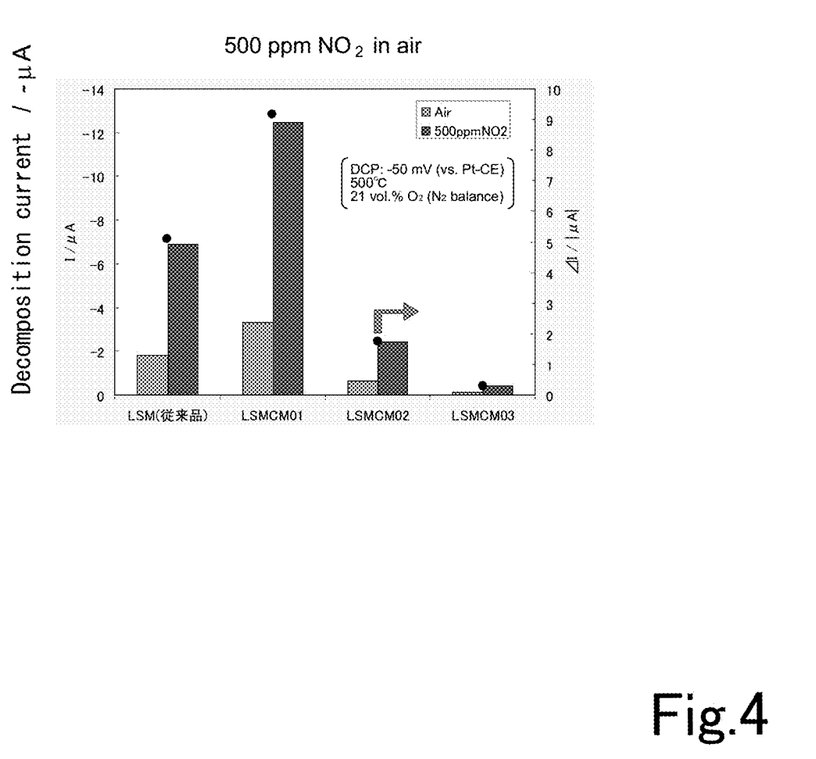
FIG. 4 shows results of NOx decomposition in an embodiment of the present invention.

As shown in FIG. 4, the sensitivity of LSMCM01 was about twice as high (ΔI=INO₂−Ibase, 9.2 μA) as the sensitivity of LSM. In other words, LSMCM01 had high selectivity and high NOx decomposition activity compared to LSM that was conventionally used. Measurement of the specific surface area of the LSMCM01 powder was 4.9 $m^2$/g, which was similar to the specific surface area of LSM. These results showed that LSMCM01 was an excellent NOx decomposition agent and was usable as a material (electrode material) for a highly sensitive NOx sensor and a material (electrode material) for a high-performance NOx decomposition device.

Figure 5:
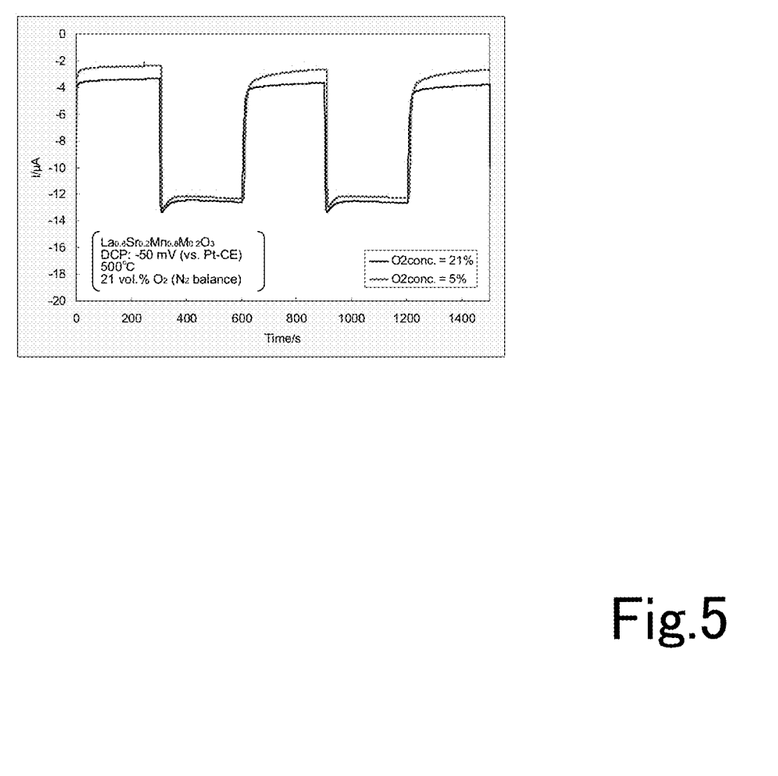
FIG. 5 shows results of evaluation of oxygen dependence of detection sensitivity exhibited by a NOx sensor in an embodiment of the present invention.

Besides, in order to study the influence of the concentration of coexisting oxygen on responsiveness to NOx, response curve measurement was conducted when the oxygen concentration of the base gas is changed from 21% to 5% in the sensor having LSMCM01 as the sensing electrode. The results are shown in FIG. 5. As shown in FIG. 5, it was confirmed that a considerable change in the oxygen concentration had little influence on responsiveness to $NO_2$. This proved that the perovskite oxide disclosed in the present specification made highly selective decomposition and detection of NOx possible regardless of the oxygen concentration.

Figure 6:
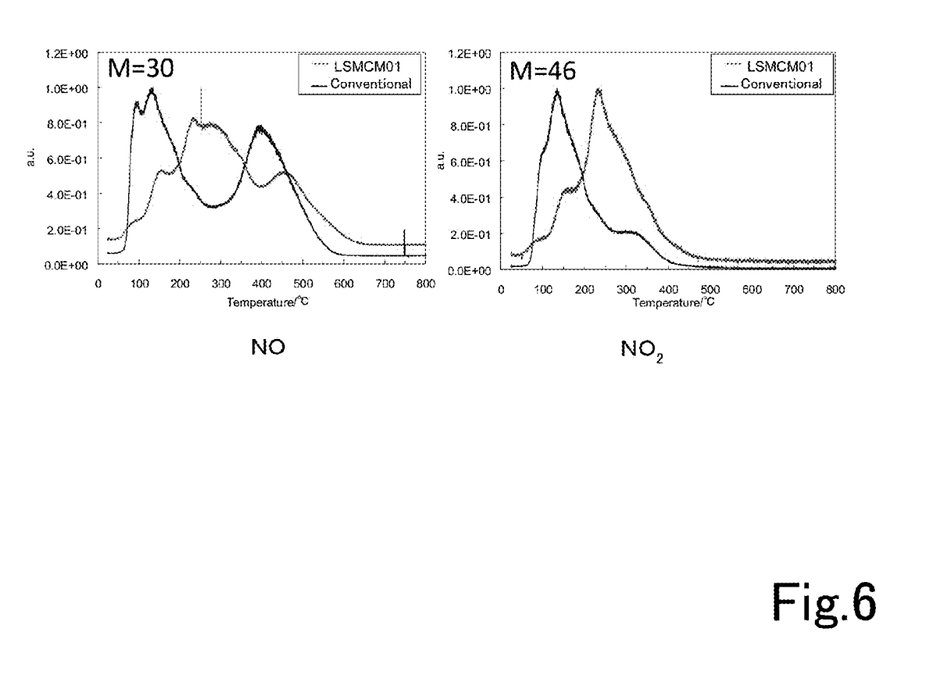
FIG. 6 shows the results of TPD measurement of a NOx sensor in an embodiment of the present invention.

Besides, LSM and LSMCM01 were subjected to TPD measurement (NO and $NO_2$) according to a conventional procedure, and the results are shown in FIG. 6. As shown in FIG. 6, LSMCM01 had a desorption peak at a high temperature and had a high desorption termination temperature compared to LSM. In other words, LSMCM01 was found to exhibit excellent NOx adsorption performance compared to LSM.

The above example proved that the NOx decomposition device of the present invention was capable of selectively decomposing NOx with high electric power usage effectiveness while suppressing influence of oxygen if present in large excess.

DESCRIPTION OF REFERENCE NUMERALS

2 NOx sensor, 10 electrochemical cell, 12 solid electrolyte, 14 first electrode, 16 catalyst phase, 18 second electrode, 20 temperature controller

The invention claimed is:

1. A NOx decomposition agent, comprising a perovskite oxide represented by:

wherein

A represents one, two, or more kinds selected from the group consisting of La, Sr, Mg, Ca, and Ba, B represents one, two, or more kinds selected from the group consisting of Ni, Fe, Co, Mn, Cr, and Cu, M represents a combination of one, two or more first metallic elements selected from the group consisting of Ti, Zr, Hf, Nb, Ta, Cr, Mo, W, and Ce, and one or two second metallic elements selected from the group consisting of Ca and Mg, the combination having a molar ratio of the first metallic element to the second metallic element such that a charge of the first metallic element and a charge of the second metallic element balance out each other, and x represents a number greater than 0 and less than 1.

2. The NOx decomposition agent according to claim 1, wherein B represents Mn.

3. The NOx decomposition agent according to claim 1, wherein M represents a combination of Ce and Mg.

4. The NOx decomposition agent according to claim 1, wherein x represents a number equal to or less than 0.2.

5. The NOx decomposition agent according to claim 4, wherein
A represents La and Sr,
B represents Mn, and
M represents a combination of Ce and Mg.

6. A NOx sensor, comprising:
an electrochemical cell that comprises:
(a) a solid electrolyte;
(b) a first electrode that comprises a NOx decomposition catalytic phase containing a perovskite oxide represented by $AB_{1-x}M_xO_3$, the first electrode being exposed to a NOx-containing gas; and
(c) a second electrode that is located to face the first electrode via the solid electrolyte interposed therebetween, the second electrode being kept from coming into contact with the NOx-containing gas;
wherein
the first electrode comprises the NOx decomposition catalytic phase that is essentially composed of the perovskite-type oxide represented by $AB_{1-x}M_xO_3$, wherein
A represents one, two, or more kinds selected from the group consisting of La, Sr, Mg, Ca, and Ba,
B represents one, two, or more kinds selected from the group consisting of Ni, Fe, Co, Mn, Cr, and Cu,
M represents a combination of one, two, or more first metallic elements selected from the group consisting of Ti, Zr, Hf, Nb, Ta, Cr, Mo, W, and Ce, and one or two second metallic elements selected from the group consisting of Ca and Mg, the combination having a molar ratio of the first metallic element to the second metallic element such that a charge of the first metallic element and a charge of the second metallic element balance out each other, and
x represents a number greater than 0 and less than 1, and
the first electrode keeps the solid electrolyte from coming into contact with the NOx-containing gas.

7. The sensor according to claim 6, wherein the first electrode consists of the NOx decomposition catalytic phase.

8. The sensor according to claim 6, wherein the first electrode is configured to be capable of being exposed to the NOx-containing gas of which oxygen concentration is not controlled.

9. The sensor according to claim 6, further comprising a temperature controller configured to control a temperature of the electrochemical cell to a predetermined temperature of equal to or greater than 400° C. and equal to or less than 800° C.

10. A method of detecting a NOx in a NOx-containing gas by using the NOx sensor according to claim 6,
the method comprising a decomposition step,
the decomposition step including decomposing NOx in the NOx-containing gas by applying a predetermined voltage between the first electrode and the second electrode of the sensor in a state where the first electrode of the electrochemical cell is exposed to the NOx-containing gas.

11. The method according to claim 10, wherein the predetermined applied voltage (the absolute value thereof) is greater than 0 mV and equal to or less than 100 mV.

12. The method according to claim 10, wherein
in the decomposition step, the electrochemical cell is operated at a predetermined temperature of equal to or greater than 400° C. and equal to or less than 800° C.

13. A NOx decomposition device, comprising:
an electrochemical cell that comprises:
(a) a solid electrolyte;
(b) a first electrode that comprises a NOx decomposition catalytic phase containing a perovskite oxide represented by $AB_{1-x}M_xO_3$, the first electrode being exposed to a NOx-containing gas; and
(c) a second electrode that is located to face the first electrode with the solid electrolyte interposed therebetween, the second electrode being kept from coming into contact with the NOx-containing gas; wherein the first electrode comprises the NOx decomposition catalytic phase that is essentially composed of the perovskite oxide represented by $AB_{1-x}M_xO_3$, wherein:
A represents one, two, or more kinds selected from the group consisting of La, Sr, Mg, Ca, and Ba,
B represents one, two, or more kinds selected from the group consisting of Ni, Fe, Co, Mn, Cr, and Cu,
M represents a combination of one, two, or more first metallic elements selected from the group consisting of Ti, Zr, Hf, Nb, Ta, Cr, Mo, W, and Ce, and one or two second metallic elements selected from the group consisting of Ca and Mg, the combination having a molar ratio of the first metallic element to the second metallic element such that a charge of the first metallic element and a charge of the second metallic element balance out each other, and
x represents a number greater than 0 and less than 1, and
the first electrode keeps the solid electrolyte from coming into contact with the NOx-containing gas.

* * * * *